United States Patent
Gray

(10) Patent No.: US 12,326,878 B2
(45) Date of Patent: Jun. 10, 2025

(54) TRAIT-BASED RELATED PERSONS SYSTEMS AND METHODS

(71) Applicant: Steven Gray, Holladay, UT (US)

(72) Inventor: Steven Gray, Holladay, UT (US)

(*) Notice: Subject to any disclaimer, the term of this patent is extended or adjusted under 35 U.S.C. 154(b) by 0 days.

(21) Appl. No.: 15/913,885

(22) Filed: Mar. 6, 2018

(65) Prior Publication Data

US 2020/0380015 A1     Dec. 3, 2020

Related U.S. Application Data

(60) Provisional application No. 62/467,249, filed on Mar. 6, 2017.

(51) Int. Cl.
*G06F 16/28* (2019.01)
*G06F 16/23* (2019.01)
*G06F 16/27* (2019.01)
*G16H 70/60* (2018.01)

(52) U.S. Cl.
CPC ........ *G06F 16/285* (2019.01); *G06F 16/2365* (2019.01); *G06F 16/27* (2019.01); *G16H 70/60* (2018.01)

(58) Field of Classification Search
CPC .... G06F 16/285; G06F 16/27; G06F 16/2365; G16H 70/60
See application file for complete search history.

(56) References Cited

U.S. PATENT DOCUMENTS

| | | | |
|---|---|---|---|
| 9,111,255 B2* | 8/2015 | Nurmi | G06V 40/161 |
| 10,025,877 B2* | 7/2018 | Macpherson | G16B 99/00 |
| 2008/0154566 A1* | 6/2008 | Myres | G16B 20/40 |
| | | | 703/11 |
| 2014/0100874 A1* | 4/2014 | Wood | G16H 10/60 |
| | | | 705/3 |
| 2018/0239866 A1* | 8/2018 | Deshakulkarni | G16B 40/00 |

* cited by examiner

*Primary Examiner* — Khanh B Pham
*Assistant Examiner* — Ranjit P Doraiswamy
(74) *Attorney, Agent, or Firm* — Steven Gray

(57) ABSTRACT

In some examples a method of diagnosing family traits is describe. the method may include, identifying family members and recording information regarding the identified family members in a first database. In some examples, the identified family members may include at least some living persons from different immediate families. sharing access to the first database with living identified family members. The method may further include updating the recorded information regarding the identified family members and analyzing the updated information regarding the identified family members. In some example, the updated information may include at least one trait of at least some of the identified family members. Some examples of the method may further include providing a summary of the analyzed information.

20 Claims, 10 Drawing Sheets

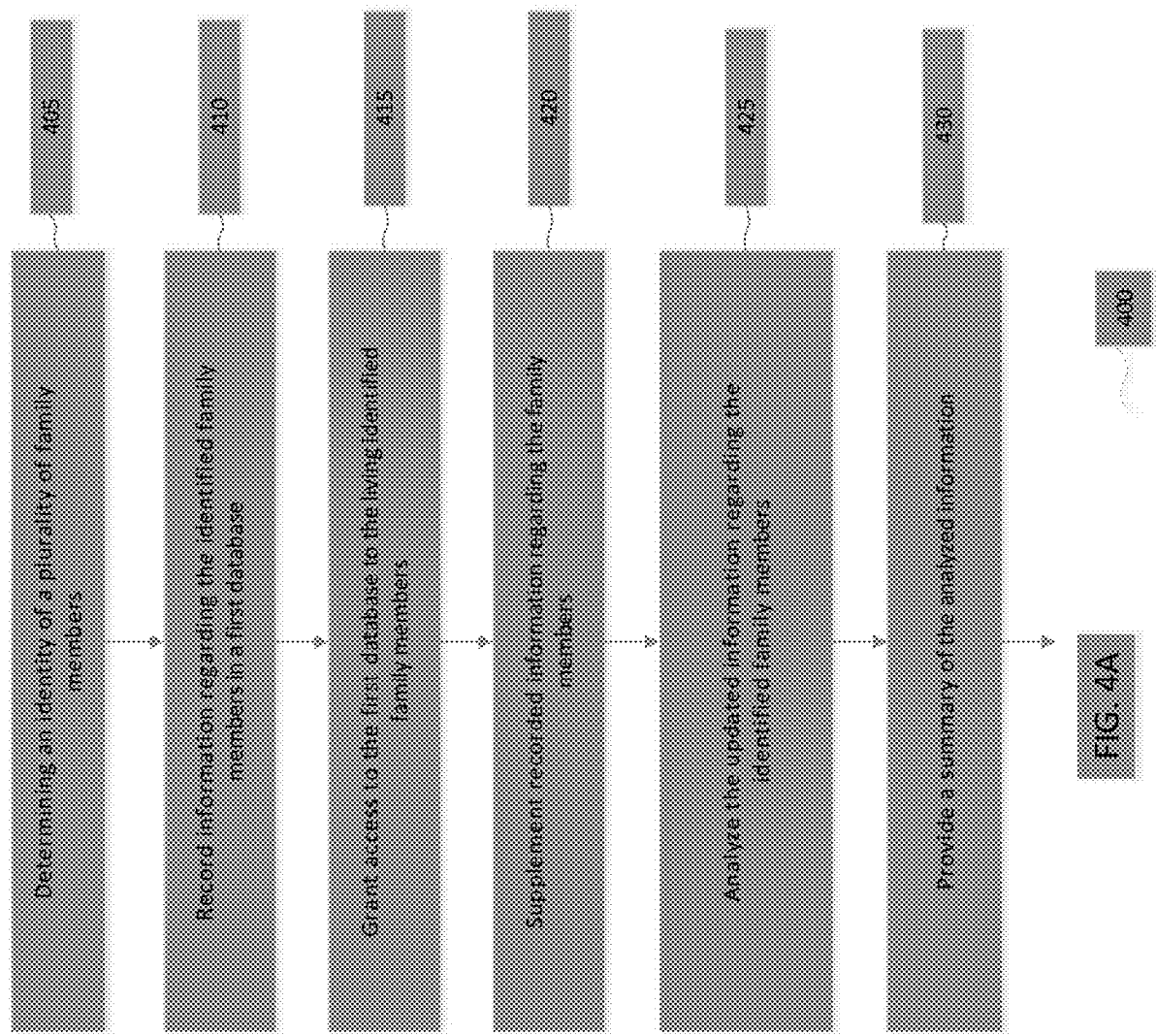

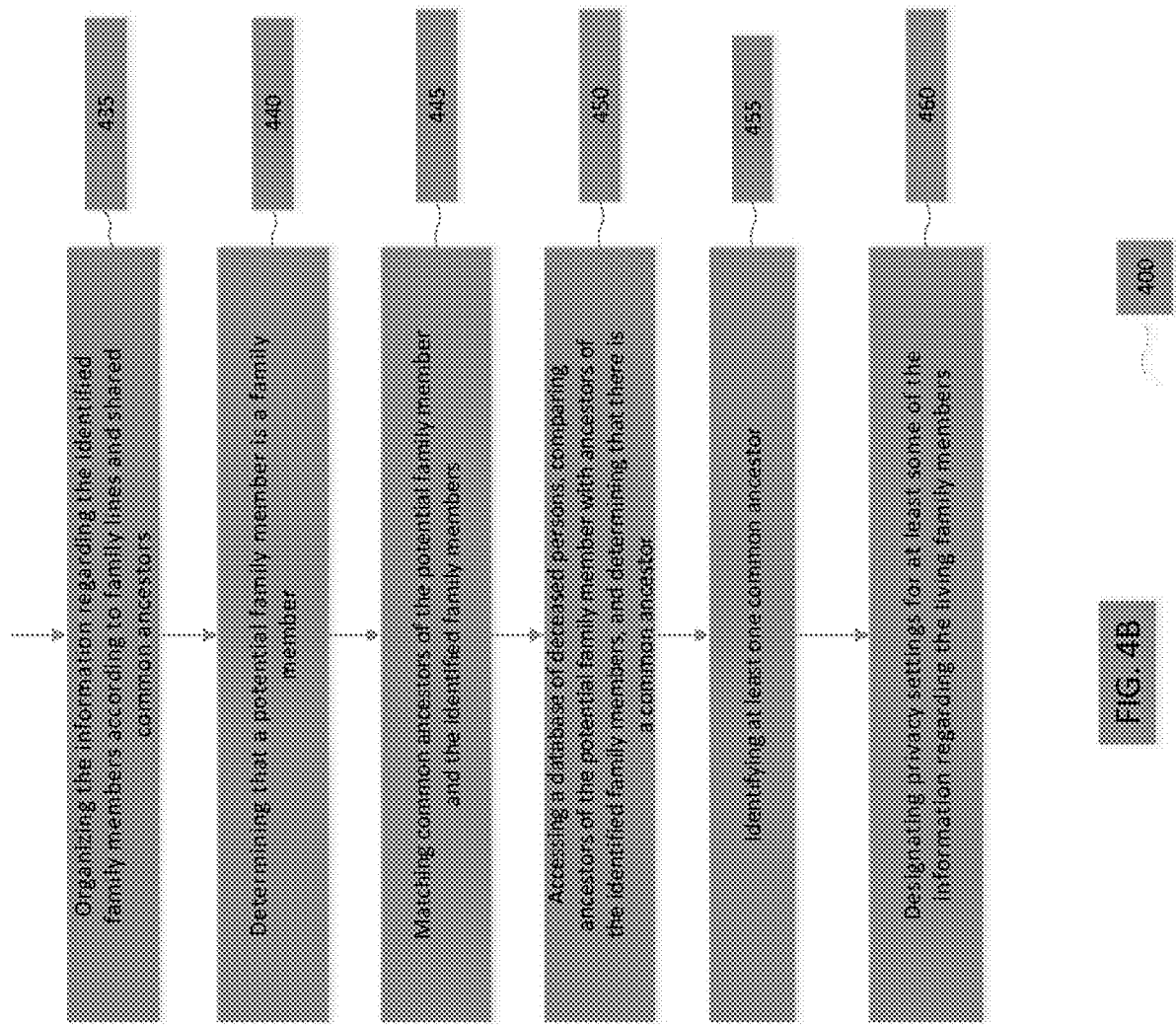

TRAIT-BASED RELATED PERSONS SYSTEMS AND METHODS

BACKGROUND

Available social networking technologies allow "linking" friends and family members but do not allow extended family connections to be made very easily. Nor do such social networking technologies provide users with any elaborate and useful analysis of data related to family and other groups. For example, many people want to communicate with their relatives, or at least know who they are, but don't know how to find them. Even if some people may know their extended family, they may not know much about them or have an idea of family characteristics/traits.

In addition, genealogical databases may not the offer the functionality to make living descendants of a common ancestor aware of each other or communicate with each other except under limited circumstances, and may not coordinate with other resources that could help link groups of people in family units. In some cases, cousins could live in the same neighborhood, pass each other at the airport, be coworkers, and meet and engage in communications that might be enhanced or different if they knew they were related beforehand. For example, someone unknowing may date his/her cousin, or separate parties may engage in a hostile encounter that might have been diffused have they known they were related. Further, many genealogy-related technologies understandably emphasize ancestry using for example databases of ancestors, but do not provide sufficient services relating to living relative.

In addition, even where persons are aware of extended family members, there are few organized medical resources that utilize such information to assist in determining an individual's propensity to certain physical illnesses or other physical traits. For example, in recent years the benefits of gene mapping has been explored. However, the practical and useful applications of such information is still too limited. In spite of existing gene databases, the information may not be adequately analyzed and provided to individuals in a very useful form—for example, relating to propensity for pre-existing conditions, etc.

SUMMARY

In one example, a method of diagnosing family traits is described. One method example may include identifying family members, recording information regarding the identified family members in a first database, sharing access to the first database with living identified family members, updating the recorded information regarding the identified family members, analyzing the updated information regarding the identified family members, and providing a summary of the analyzed information. In one example of the method, the updated information may include at least one trait of at least some of the identified family members, and the identified family members may include at least some living persons from different immediate families.

In one example of the method, identifying the family members may include importing data from a second database. In one example, the second database may be related to at least one of a social networking database and a genealogical database. In another example, the method may include authenticating the recorded information.

In an example of the method the identified family members may have different classifications. In one embodiment, the classifications may include different levels of family members. For example, in one specific embodiment, the levels of family members may include level one family members, which may be members of an immediate family, level two family members, which may have at least one shared grandparent with the level one family members, and level three family members, which may have at least one shared great grandparent with the level one family members. In that embodiment, the step of identifying the family members may include identifying level one family members before identifying level two family members, and identifying level two family members before identifying level three family members; and the step of recording information may include recording information regarding the identified level one family members before recording information regarding the identified level two family members, and recording information regarding the identified level two family members before recording information regarding the identified level three family members. In a further embodiment of the method, the levels of family members may also include at least level four family members and level five members. In an embodiment, the database may include recorded information of identified family members of different family groups, and the recorded information of identified family members of different family groups may be mergeable—for example, upon discovering a common ancestor between different groups. Thus, the identified family members may share at least one common ancestor.

In an example of the method, the step of updating may include determining traits of the identified family members. In one embodiment, determining traits may include at least one of identified family members responding to a questionnaire, genetic testing by identified family members, and a third party supplying traits regarding identified family members. In a related embodiment, the third party may include at least one of a medical provider and an insurer. In another related embodiment, the traits may include at least one of a biological characteristic, a socio-economic characteristic, an ideological characteristic, and a life decision. In a further embodiment, the biological characteristic may include at least one of a physical characteristic, a race, a gender, a gene marker, and a diagnosis of an illness, disease, or disorder. In a related embodiment, the illness, disease, or disorder may include Thalassemia, sickle cell anemia, haemophilia, cystic fibrosis, Tay Sachs disease, fragile X syndrome, Huntington's disease, Angelman Syndrome, diabetes, cancer, alcoholism, auto-immune diseases, and schizophrenia. In another related embodiment, the socio-economic characteristic, ideological characteristic, and life decision may include at least one of an education level, a profession, a political affiliation, a religious persuasion, an associated organization, a marital status, a criminal history, an alma matter, a past or present domicile. In one example of the method, the summary of the analyzed information may include a diagnosis of potential medical risks and recommended preventative actions.

An example of the method may also include organizing the information regarding the identified family members according to family lines and shared common ancestors. In an embodiment of the method, identified family members may have access to the identities of other identified family members. A related embodiment of the method may include the steps of a potential family member inputting information in the database, and determining that the potential family member is a family member.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein—including their organization and method of operation—together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

FIG. 4A is a flow chart illustrating an example of a method relating to diagnosing traits, in accordance with various aspects of this disclosure.

FIG. 4B is a flow chart illustrating an example of the method of FIG. 4A relating to family traits, in accordance with various aspects of this disclosure.

DETAILED DESCRIPTION

Figure 1:
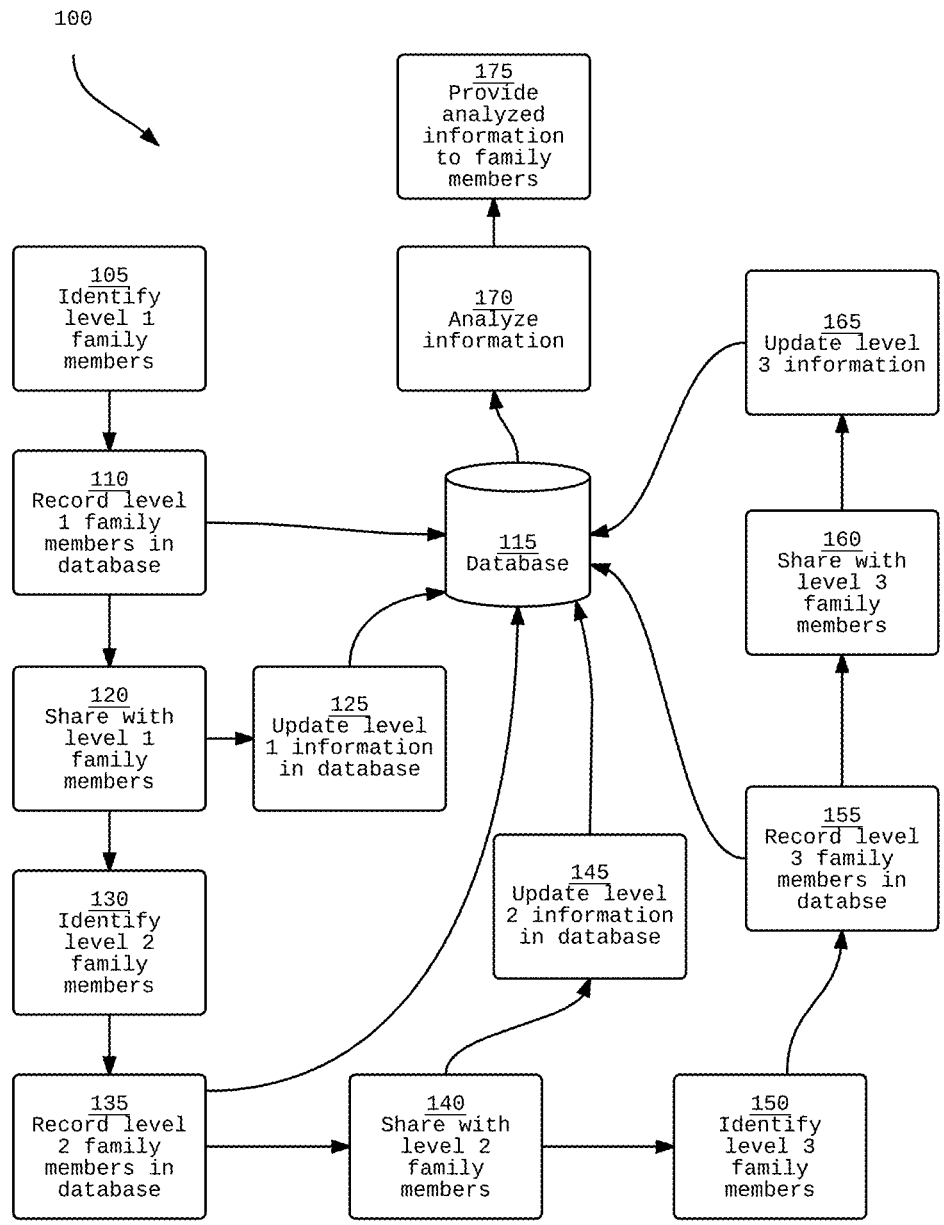
FIG. 1 shows a flow chart relating to a trait-based family member database, in accordance with various aspects of this disclosure.

"Gene mapping" is described herein to mean the identifying of one or more of a person's genes.

There are a variety of reasons why prior art systems, methods, programs, databases, etc., do not have the functionality of allowing descendants of common ancestors to utilize information relating to such descendants in useful ways (such as for example providing means of contact one another). For example, privacy concerns, and liability stemming from divulging personal identifying information against a person's consent, may be some such reasons.

Regardless of the specific reasons, technology surrounding gene mapping is relatively new and thus it is extremely difficult in most cases to obtain the actual gene maps of deceased individuals. It has been historically difficult to obtain a sufficiently large pool of related individuals' gene maps. Conceivably this may be due in part to the fact that, in many places, such information is considered highly personal, private, and protected accordingly. In addition, in some jurisdictions, individuals might be discouraged from becoming aware of particular genes relating to preexisting conditions and imply significant treatment-related expenses (e.g., and lead to the imposing of higher health insurance premiums). Yet effectively treating preexisting conditions, potentially in advance of worsening symptoms, is desirable, and a potential benefit of gene mapping analyzing a group of persons with a common gene pool ancestry.

Another reason persons may be reluctant to share health-related information such as for example their genetic maps is lack of an incentive to do so. In other words, the mere possibility that learning and sharing such information may help someone (including him/herself), may not provide sufficient motivation for action. For example, some may suppose that the risk of having a detrimental condition is so small that it is not worth the effort of seeing a doctor and having potentially revealing medical tests performed. In addition, some may be embarrassed by some medical condition and may not want others to learn of it. Or some may simply be unaware of the extent of any benefits that sharing such information could have on other family members. In some cases, although some may have a genetic predisposition to some terminal illness, rather than worry about such a condition and undergo potentially painful and at least inconvenient treatment, some would simply rather live in ignorance as long as possible.

Prior art systems and methods have lacked sufficient incentives for individuals to consent to allow living relatives to use their medical information in useful ways. Moreover, such consent has often been an "all of nothing" approach without sufficient alternatives for protecting personal identifying information to at least some extent, while still allowing certain medical information to be shared (e.g., anonymously to a group) in useful way. Similarly, prior art systems have lacked proper incentives for persons to consent to divulge their genetic maps. Also, creating a database with genetic information regarding health conditions may require a fair amount of strategical organization, potential collaboration, and the intertwining of various elements into a single cohesive system that has presented discouraging challenges hitherto not sufficiently overcome by the prior art.

Systems of protecting such information have also not fully utilized the option of identifying and contacting relating persons to request consent to use certain valuable information in useful ways. And this is spite of advances in social media technologies that have made it easier to identify and connect living persons. For example, methods and systems exist for connecting persons by professional, educational, and/or civic relationships, and/or even for connecting persons who casually meet for the first time. Although individuals are presented with an abundance of such networking options, such options may not provide an optimally effective and convenient forum and/or platform for organizing relationships from the family-relationship perspective, as they may not be targeted toward nor provide the tools necessary for organizing individuals in family groups, and then using that information in useful ways to benefit that group. Relatedly, such networking options may not adequately facilitate finding and/or identifying and/or communicating with living relatives—e.g., persons who may be related by common ancestors (whether adopted or by blood)—nor facilitate the utilization of such family-related information.

Described herein may be techniques, methods and/or systems for identifying and/or connecting related persons. In one aspect the disclosure may have primary application for living persons with common ancestors. Some examples of the disclosure may relate to creating a database and organizing individuals into family groups and relationships. Some examples may also relate to utilizing associated information—whether found in such created or existing databases of living persons—for medical purpose. Some examples of the disclosure may relate to taking information from existing databases (e.g., with the consent of individuals), organizing it in more useful and presentable ways, and potentially supplementing the information (for example, by the same individuals associated with the information). In some examples, whether using existing and/or created databases, analytics may be used to determine whether and how different persons are related, including identifying common ancestors, and then use such information as a springboard for more detailed information and analysis.

The following description provides examples and is not limiting of the scope, applicability, and/or examples set forth in the claims. Changes may be made in the function and/or arrangement of elements discussed without departing from the scope of the disclosure. Various examples may omit, substitute, and/or add various procedures and/or components as appropriate. For instance, the methods described may be performed in an order different from that described, and/or various steps may be added, omitted, and/or combined. Also, features described with respect to some examples may be combined in other examples.

FIG. 1 shows a flow chart 100 relating to a trait-based family member database 115, in accordance with various aspects of this disclosure. At block 105, level 1 family members may be identified. In some examples, level 1 family members may be immediate family members. In one examples, level 1 (and other level) family members may be related by blood. In one example, level 1 (and other level) family members may be based at least in part, or based, on legal status of one or more common ancestors—for example, two or more family members may be the son(s) or daughter(s) of common parents shown for instance, by census and/or other government and/or other records. In some examples, the level 1 (and other level) family members may be based at least in part, or based, on either blood or legal/other status, and such a distinction may in some examples be noted. At block 110, the level 1 family members may be recorded in the database 115. At block 120, access to the database 115 may be shared with the level 1 family members. In some examples, the level 1 members may receive an auto-generated email informing them of the database 115.

At block 125, level 1 information may be updated in the database. In some embodiments, the update may occur by the level 1 family members entering their requested information in the database (using for example, a questionnaire and/or survey). In some examples, such information may relate to physical/health traits and medical information. In some cases, the family members may be invited to participate in testing related to and for gathering the desired requested information. In some examples, such testing may relate to determining certain genes and/or gene markers of the family members, including identifying mutated genes (and in some examples may involve/place greater emphasis on mutations affecting the coding region of genes). In addition, the information may be updated more than once and many times over a period and potentially throughout a lifetime and after. In some examples, the information may also be updated by third parties.

At block 170, the information in the database 115 may be analyzed. In some examples, the analysis may include comparing the information of different family members (e.g., level 1 family members). In some examples, analyzing information may involve comparing the information of different family members (and/or e.g., a subset of family members) that are related by blood, or by legal status with respect to a common ancestor, or by both, or of family members that have certain commonalities (e.g., sex, geographical origination, etc.). In some examples, the analysis may include associating a phenotype with a genotype for individuals and/or groups of related persons. At block 175, the analyzed information may be provided to family members. Providing the analyzed information to family members may involve determining which analyzed information to provide. In some examples, determining what information to provide may be based on (or based at least in part on) designated/selected areas of interest based on the preferences of family members, and/or based on the results of the analyzed information itself. In some examples, determining what information to provide may be based on a level of consent of a particular individual (as further described below). In some examples, the analysis may result in discovery of certain areas of particular interest and/or "red flags," which may have a higher priority/greater level of interest for family members. Different family members may want to learn about different analyzed information. In some examples, the provided analyzed information may be anonymous regarding specific family members. For instance, a family member may receive a summary report noting characteristics and/or traits of all and/or a certain subset of family members by percentages or by ratios (e.g., "3/7 level 1 family members have . . . "). In some examples, analysis may involve distinguishing between de novo and inherited mutations.

At block 130, level 2 family members may be identified. At block 135, level 2 family members may be recorded in the database 115. At block 140, access to the database 115 may be shared with all or some level 2 family members. At block 145, level 2 information may be updated in the database 115. At block 150, level 3 family members may be identified. At block 155, level 3 family members may be recorded in the database 115. At block 160, access to the database 160 may be shared with level 3 family members. At block 165, level 3 information may be updated. The analyzed information 170, as described above, may include information specific to level 1 family members, level 2 family members, level 3 family members, and any number of additional levels of family members, and general and/or specific subsets thereof.

In some examples, the step of analyzing information 170 may include analyzing information between more than one family group. For example, one family group may have certain characteristics, and another family group may have similar or different characteristics. Analysis 170 may include determining whether such commonalities or differences may be owing to certain factors. For example, perhaps both family groups carry a certain mutated gene with a certain frequency, and the ancestry of the groups share some common region of origin (for example, certain ancestors originated from the same town during a same period).

Figure 2:
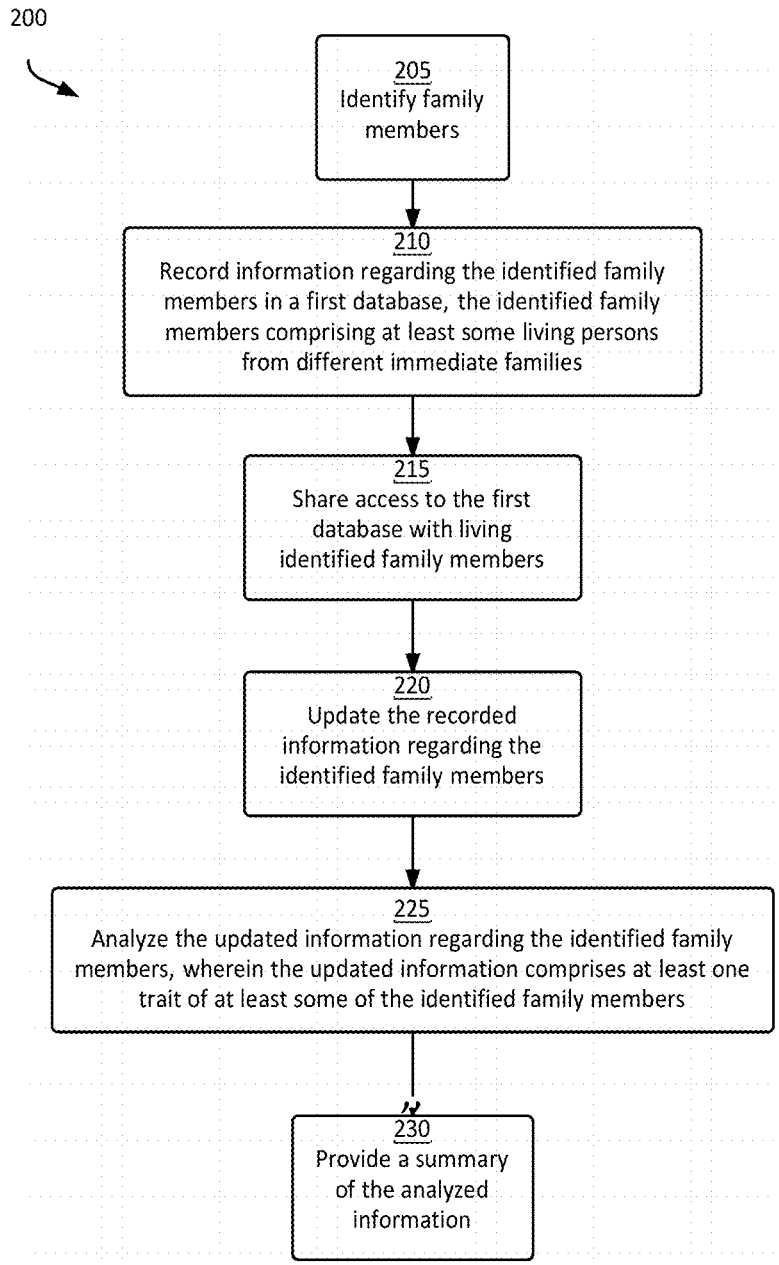
FIG. 2 is a flow chart illustrating an example of a method relating to diagnosing family traits, in accordance with various aspects of this disclosure.

FIG. 2 is a flow chart illustrating an example of a method 200 relating to diagnosing family traits, in accordance with various aspects of this disclosure. At block 205, the method 200 may include identifying family members. At block 210, the method 200 may include recording information regarding the identified family members in a first database, the identified family members including at least some living persons from different immediate families. At block 215, the method 200 may including sharing access to the first database with living identified family members. At block 220, the method 200 may include updating the recorded information regarding the identified family members. At block 225, the method 200 may include analyzing the updated information regarding the identified family members, wherein the updated information may include at least one trait of at least some of the identified family members. At block 230, the method 200 may include providing a summary of the analyzed information.

Figure 3:
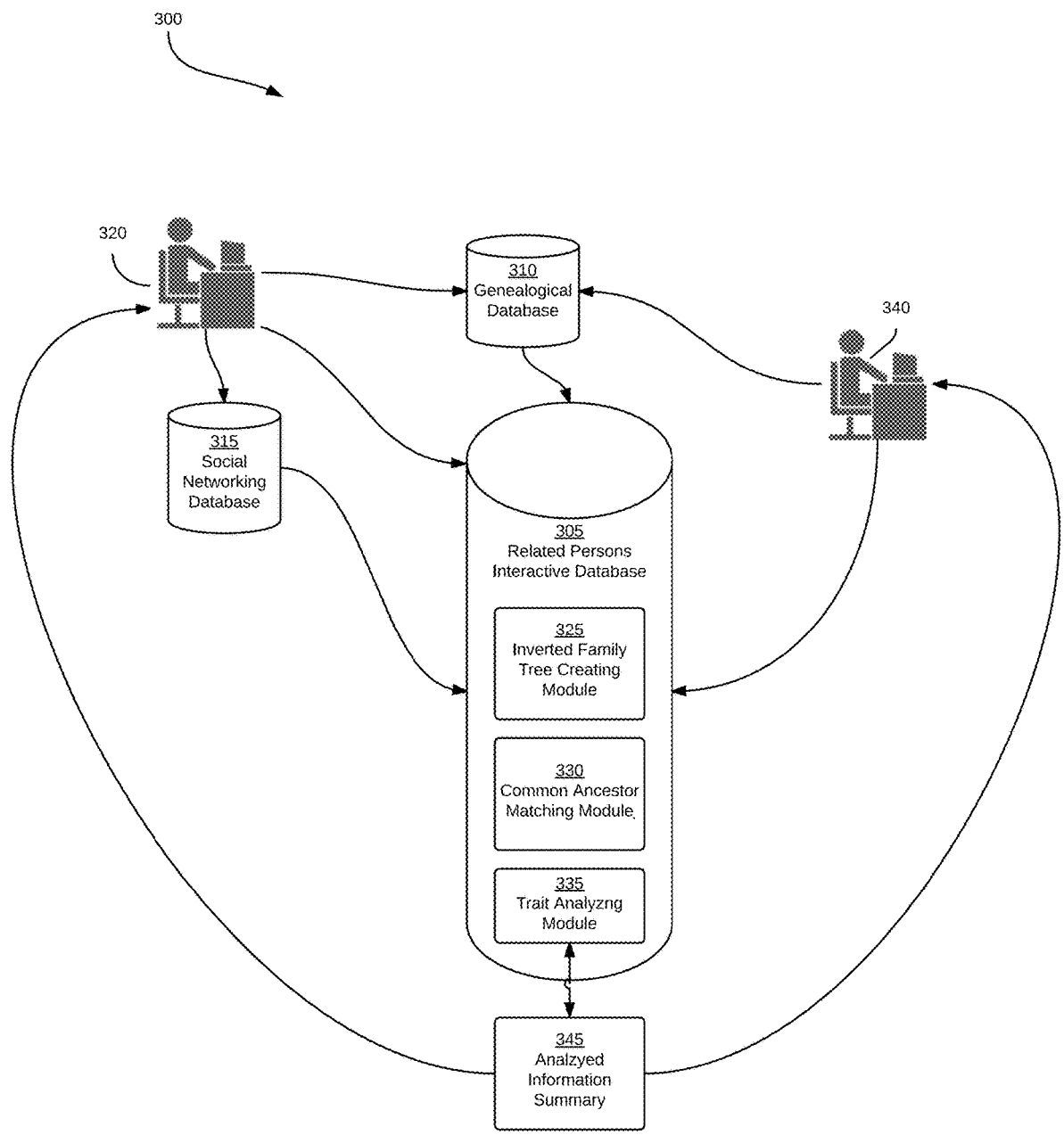
FIG. 3 is an illustration of an example of a system relating to a trait-based related persons interactive database, in accordance with various aspects of this disclosure.

FIG. 3 is an illustration of an example of a system relating to a trait-based related persons interactive database, in accordance with various aspects of this disclosure. The system may include a related persons interactive database 305. The database may include various modules, processors, circuits, and/or other structures for performing relevant functions, including for example, an inverted family tree creator 325, a common ancestor matcher 330, and a trait analyzer 335. Users 320, 340 of the database 305 may input or caused to be inputted; or information related to users 320, 340, may be inputted into the database. In some examples, the inputted information may include identities of living related persons and some examples may include identities of deceased related persons. Such information may also come from a variety of sources including for example and without limitation a genealogical database 310, and/or a social networking database 315. Example genealogical databases may include Family Search, Ancestry, Roots, etc., while example social networking databases may include Facebook, LinkedIn, Google Circles, etc. Based on the inputted and other information in the database 315, the information may be analyzed 345 and provided to the users 320, 340, among others. In some examples, the analyzed information may indicate that users 320, 340, are related.

In one example, an application may be provided, which may allow contacts from a social networking database to be sorted according to different family member levels. For example, in one variation, social networking profiles (represented for example by a box containing a photo and name) may be dragged and dropped according to a certain hierarchy. For instance, level 1 family member (e.g., immediate family members such as sisters, brothers, parents) profiles may be organized together, and all level 2 family member (e.g., first cousins, aunts, uncles, etc.) profiles may be also be organized, level 3 family members etc., in a "family tree" or another suitable format. In some examples, and based at least in part on preferences and privacy settings, such a family organization tree may be shared and viewable by others (for example friends of a level 1 family member). In some examples, due for example to privacy concerns, specific identifying information of particular members of the family organization tree may not be viewable by non-family members, or distant-level family members, or may be based on the particular level of a family member (as further explained below).

FIG. 4A is a flow chart illustrating an example of a method 400 relating to family traits, in accordance with various aspects of this disclosure. Similar in some aspects to FIG. 2, at block 405, the method 400 may include identifying a plurality of family members. At block 410, the method 400 may include recording information regarding the identified family members in a first database. In some examples, the identified family members may include at least some living persons from different immediate families. At block 415, the method 400 may including granting access to the first database to the living identified family members. At block 420, the method 400 may include supplementing the recorded information regarding the identified family members. At block 425, the method 400 may include analyzing the updated information (which may include the supplemented information) regarding the identified family members. In some examples, the updated information may include at least one trait of at least some of the identified family members. At block 430, the method 400 may include providing a summary of the analyzed information.

FIG. 4B is a flow chart illustrating an example of method 400 relating to family traits, in accordance with various aspects of this disclosure. At block 435, the method 400 may include organizing the information regarding the identified family members according to family lines and shared common ancestors. In some example, the identified family members have access to the identities of other identified family members. At block 440, the method 400 may include determining that a potential family member is a family member. For example, the determining 440 may include determining that a potential family member belong to a same family group as the plurality of family members. For example, the information recorded at 410 may be inputted by a potential family member, and based at least in part on that inputting, the determination 440 may be made that the potential family member is one of the identified family members. In some examples of the method 400, the determining 440 may include at block 445 matching common ancestors of the potential family member and the identified family members. In some examples of method 400, matching common ancestors 445 may include the steps at block 450 of accessing a database of deceased persons, comparing the ancestors of the potential family member with ancestors of the identified family members, determining whether there is a common ancestor. In some examples, at least some of the deceased persons may include ancestors of both the potential family member and the identified family members.

At block 455, the method 400 may include identifying at least one common ancestor. In one example, more recent ancestors may be identified first. In some examples, more than one common ancestor may be identified. In some examples, the descendants of the common ancestors may be directed to information regarding the common ancestor (e.g., birthplace, date of birth, death date, marriage date, baptism date, life history, photos, etc.). In another related embodiment, the matching 445 and other operation may include utilization of analytics. In some examples, the method 400 may include at block 460 designating privacy settings for at least some of the information regarding the living family members.

Figure 5:
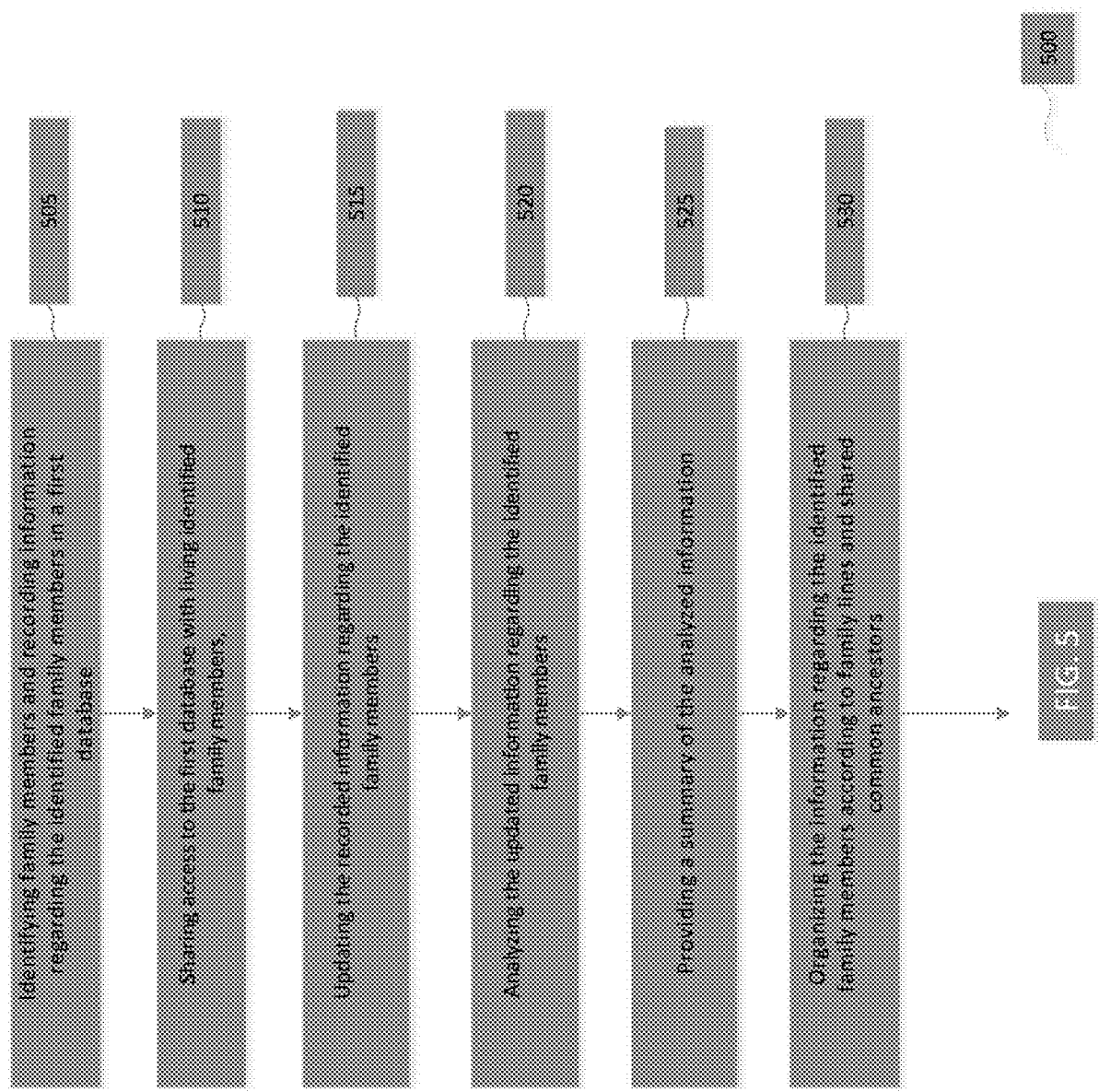
FIG. 5 is a flow chart illustrating an example of a method 500 relating to forming family connections, in accordance with various aspects of this disclosure.

FIG. 5 is a flow chart illustrating an example of a method 500 relating to forming family connections, in accordance with various aspects of this disclosure. Relatedly, a method of connecting relatives may be described. The method 500 may include at block 505 identifying family members, which may include in some examples recording information regarding the identified family members in a first database.

In some examples, the identified family members may include at least some living persons from different immediate families. In some examples, the method 500 may also include at block 510 sharing access to the first database with living identified family members. In some examples, the method 500 may also include at block 515 updating the recorded information regarding the identified family members. In some examples, the method 500 at block 520 may also include analyzing the updated information regarding the identified family members. In some examples, the updated information may include at least one trait of at least some of the identified family members. In some examples, the method 500 may also include at block 525 providing a summary of the analyzed information. In some examples, the method 500 at block 530 may include organizing the information regarding the identified family members according to family lines and shared common ancestors.

In some example, identified family members may have access to the identities of other identified family members. In some examples, the method may include a potential family member inputting information in the database, and determining that the potential family member is a family member. In some examples, the determining may include matching common ancestors of the potential family member and the identified family members. In some examples, the matching common ancestors may include accessing a database of deceased persons. In some examples, the at least some of the deceased persons may include ancestors of both the potential family member and the identified family members. In some examples, the matching common ancestors may include comparing the ancestors of the potential family member with ancestors of the identified family members, determining whether there is a common ancestor; and identifying at least one common ancestor.

It should be noted that methods 200, 400, 500 are just some implementations and that the operations of the methods 200, 400, 500 may be rearranged or otherwise modified such that other implementations are possible, and utilizing other steps based on the claims below and based on the steps and operations described with regard to any of the figures described herein.

Figure 6:
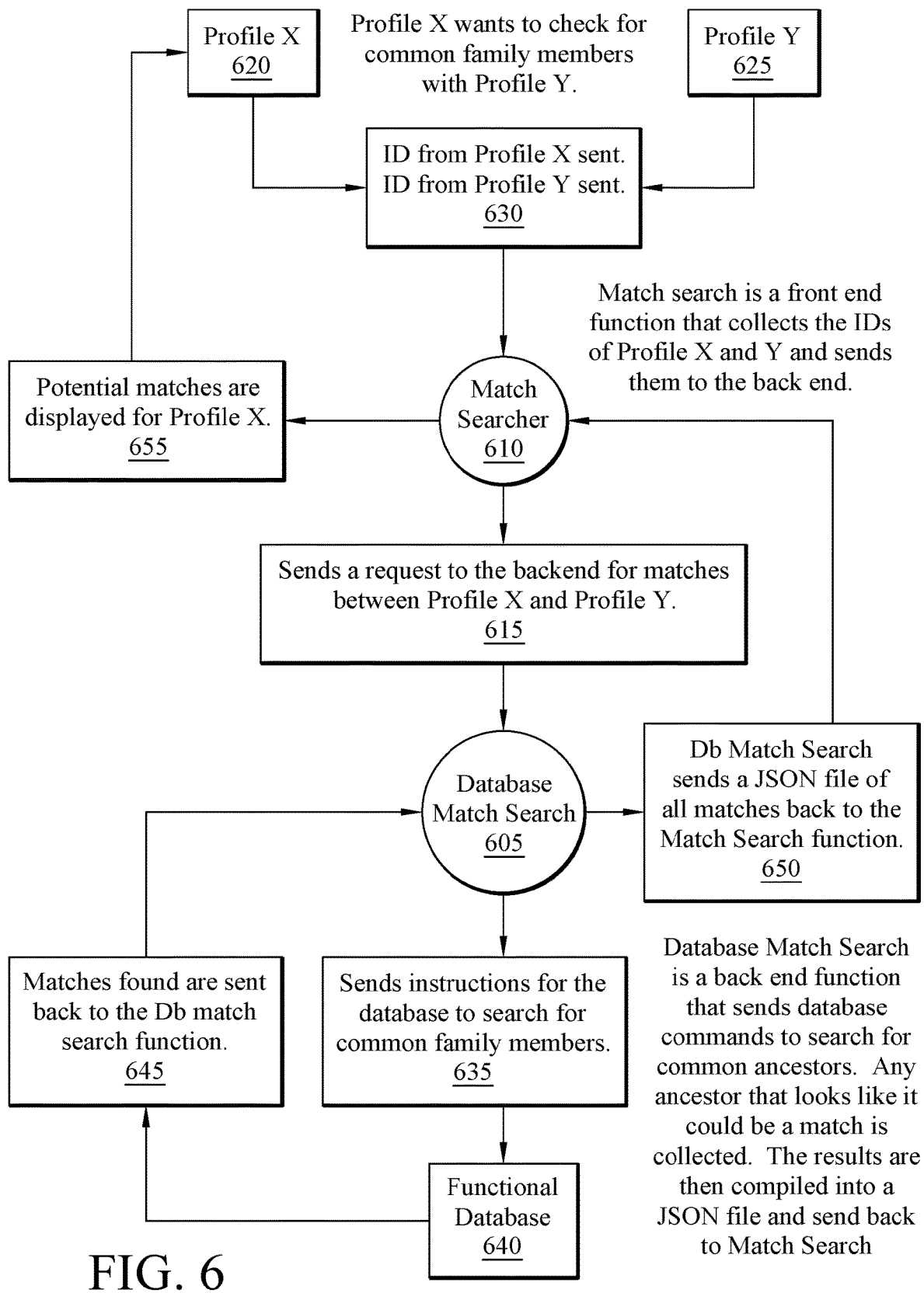
FIG. 6 illustrates an example system 600 that may utilize algorithms for finding common ancestors, in accordance with some aspects of the present disclosure.

FIG. 6 illustrates an example system 600 that may utilize algorithms for finding common ancestors, in accordance with some aspects of the present disclosure. In one example, the identities of a first person's living relatives that may have a common ancestor with a second person may be ascertained. For example, a user associated with profile X 620 may be able to determine whether she/he shares common family members with a user associated with Profile Y 625.

The system 600 may include a match searcher 610. The match searcher 610 may perform front end function such as collecting identifying data of Profile X 620 and Profile Y 620 and transmitting such identifying data to back end destinations where back end operations may be performed. For examples, at block 630, some form of identifying data for Profile X 620 and some form of identifying data from Profile Y 625 may be transmitted to the match searcher 610. At block 615, the match searcher 620 may send a request to the backend/database match searcher 605 for matches between Profile X 620 and Profile Y 625.

In some examples, the system 600 may include a database match searcher 605, which may in some embodiments be a back end function that sends database commands to search for common ancestors. The database match searcher 605 may collect any ancestor that potentially could be a match by for example, at block 635, sending instructions to a functional database 640 to search for common family members.

At block 645, any found matches found may transmitted back to the database match searcher 605. At block 650, the database match searcher 605 may further compile the results into for example a JavaScript Object Notation (JSON) file to be sent to (or back to) the Match Searcher 610. At block 655, potential matches of common ancestors may be displayed for Profile X 620.

Different examples may involve using one or more algorithms to facilitate and enable such searching and matching. For instance, it may be determined that a first person, e.g., user 320, with ancestry information already inputted in the related persons interactive database 325 (whether by manual input of the first person or whether obtained through a genealogical database 310), shares a common ancestor with a second user, e.g., user 340.

For example, the common ancestor may be a grandparent, or a great-great-great grandparent. In some instances, the first person may not share a common ancestor by blood or by grandparent (but non-blood) status, but may nevertheless have a common relative (such as through marriage), which may also be discovered using the common ancestor matcher 330. The analyzed information summary 345 may include information such as how many ways the first person and the second person are related, how distantly the first person and the second person are related first, second . . . eleventh cousins), as well as include information regarding the identity of the common ancestor. For example, in one variation, the first person and the second person may be sent a link to a "Memories" profile available through FamilySearch.org, associated with the common ancestor.

In some examples, a common ancestor of a first person and a second person may not be ascertained. Nevertheless, additional information regarding friends and or contacts of the first person may be known, for example, through information provided or based at least in part on a social networking database 315. Assuming that ancestry information is known regarding the friends and/or contacts of the first person, the common ancestor matcher 330 may also determine whether those friends and/or contacts of the first person have common ancestors with the second person, and this information may also be provided to the first person and/or the second person. For example, a first coworker may know or be friends with (e.g., "friends" on Facebook) the cousin of a second coworker, and the connection may be made although the first coworker is not related to the second coworker.

Figure 7:
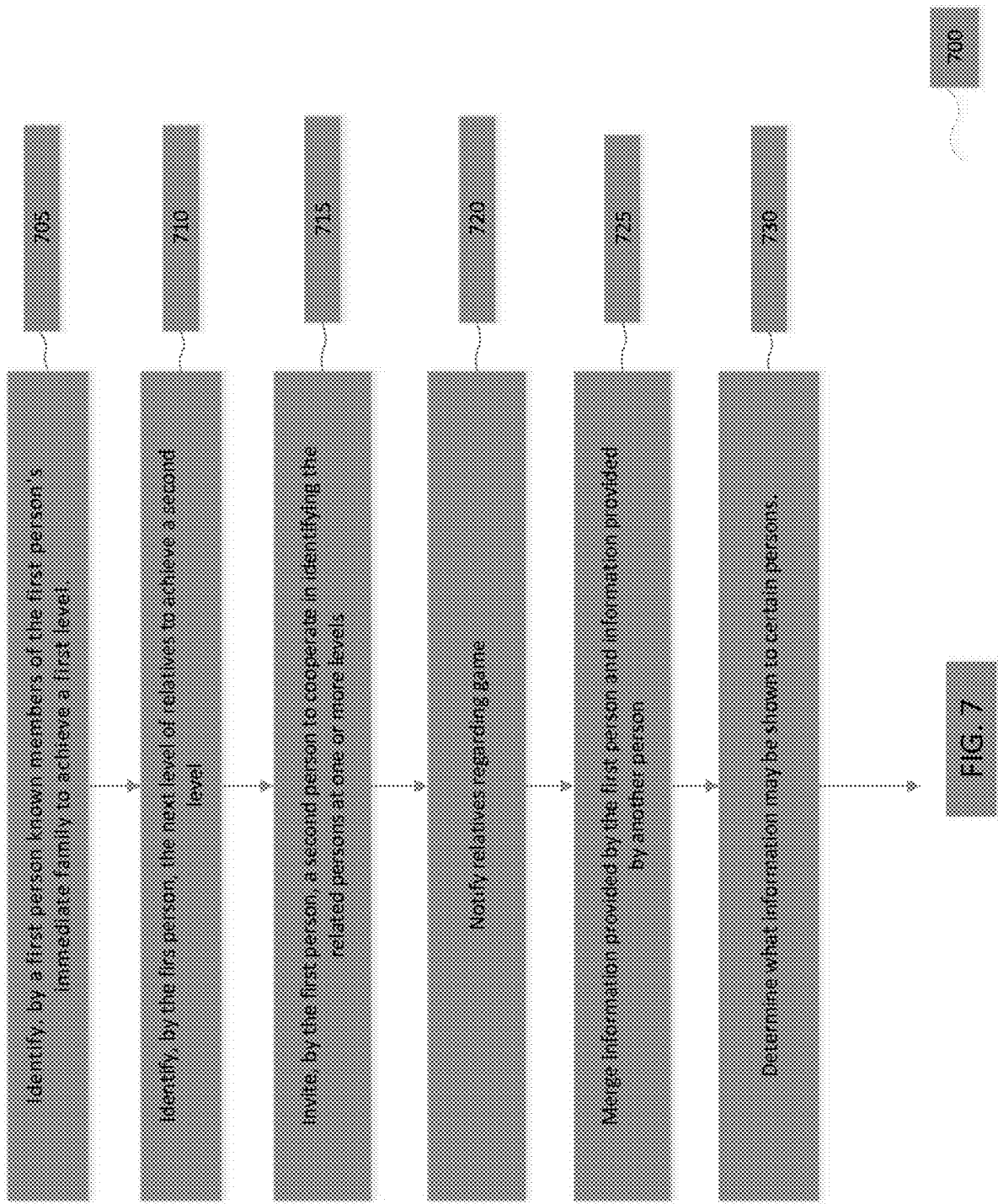
FIG. 7 illustrates a method for creating a family database relating to common ancestors, in accordance with some aspects of the present disclosure.

FIG. 7 illustrates a method 700 for creating a family database relating to common ancestors, in accordance with some aspects of the present disclosure. In some examples, a family database may be created through a type of challenge or game, as follows. The method 700 may include at block 715, a first person identifying known members of the first person's immediate family—e.g., father, mother, and children (regardless of whether the first person is the father, mother, or child of the immediate family). In some examples, once all such immediate family members are identified, a "first level" may be achieved. Next, the method 700 at block 710 may include the first person identifying the next "level" of relatives—e.g., either the mother and/or the father's mother and/or father (i.e., the grandfather and grandmother), sisters and/or brothers and offspring of the sisters and/or brothers). In some examples, after all such known individuals have been identified on either side (i.e., the mother or the father's), the "second level" may be achieved. Once all such known individuals are identified on both sides, the "third level" may be achieved, and so on.

Although the first person alone may take up the challenge of identifying relatives and achieving different levels, the challenge/game may also be a team endeavor. For example, at block 715, the method 700 may include a first person inviting a second person to cooperate to identify the related persons at each level. In some examples, block 715 may include the first and second persons cooperating as described. In some examples, the first person and the second person may be related spouses, siblings, etc.). In some examples, all the identified members of a family may work together in identifying relatives.

Once a first, second, and/or third level, as described above, is achieved, a "fourth level" may follow. The fourth level may be achieved by identifying the father and mother of either the grandfather or the grandmother, as well as all the progeny, including the living progeny, of the said great-grandfather and great-grandmother.

In some examples, the method 700 may include at block 720 sending a notification to other relatives regarding the progress of the game, including levels attained. In some examples, notifications may include consents to use all or some information, and include authentication operation to for example verify information that has been inputted. In one embodiment, in order for each level to be achieved, every individual may be required to consent to allow the other members of that level to know his/her identity (name, etc.). In one embodiment, an individual may determine which level of persons is allowed to know his/her identify. In another embodiment, an individual may be able to determine which particular persons of a particular level are allowed to know his/her identity.

In some examples, the method 700 may include at block 725 merging information provided by the first person, and other related information provided by a second person to for example, attain additional levels. In some examples, it may not be necessary for the first person alone to notify and/or identify all the members of the family about the game. For example, another person (including for example the second person), who may potentially be related in some way to the first person, may have also identified all the members the that other person's immediate family, and thus the first person and second person may share/join information, allowing each to achieve or come closer to achieving additional levels.

In some examples, the method 700 may include at block 730 determining what information may be shown to certain persons. In some examples, such determining may be based at least in part on any previous consents and levels of consents provided by particular family members. In some examples, such determining may be based on certain privacy laws pertaining to a particular jurisdiction. For example, to address privacy concerns, in one embodiment an individual need only be "identified" with limited and more-generic information ("identity-obscured person")—for example, sex and approximate age (10-20 years for example), and general location of domicile (e.g., country). If a person related to the identify-obscured person wishes to contact or know with greater specificity the identity of the identity-obscured person, in one embodiment a means/communication paths may be provided for contacting the identity-obscured person to make such a request (without disclosing the identity of the identity-obscured)—such as an email without containing identifying information—which may be denied by the identity-obscured person. In addition, in one embodiment, the identity-obscured person may opt to not receive any such requests.

Figure 8:
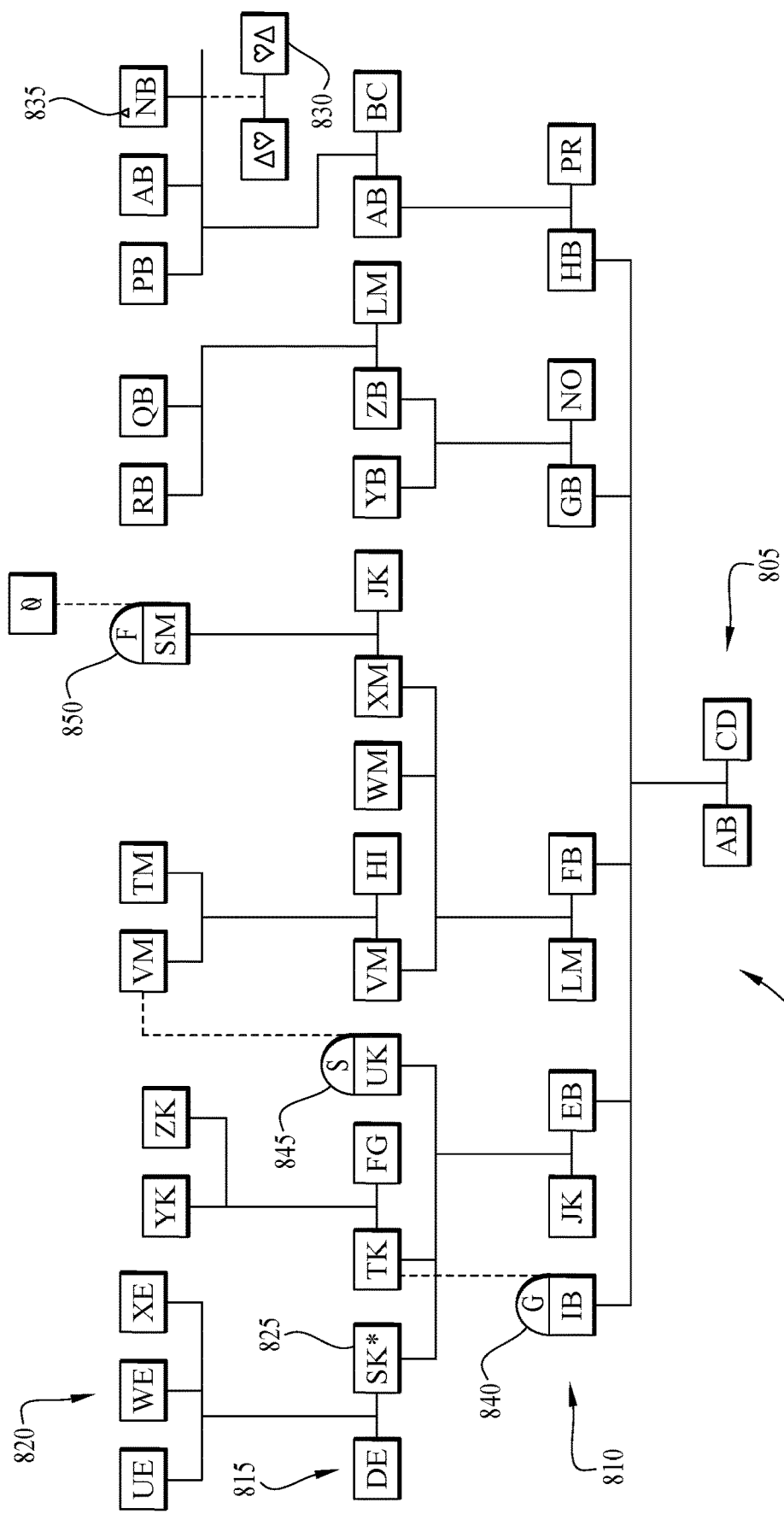
FIG. 8 illustrates a screenshot of an example webpage of a website, in accordance with some aspects of the present disclosure.

In one embodiment, the method and/or system described may be used to form a database. In one embodiment, such a database may be accessible on a website. For instance, FIG. 8 illustrates a screenshot of an example webpage of a website, in accordance with some aspects of the present disclosure. In some examples the database may present information in the form of an inverted tree. For example, the family tree may become much larger with more recent generations of persons. In some examples, the inverted family tree may be a more holistic database than prior genealogical databases. For instance, in some examples the database may not list only mother, father, and children and legally sanctioned partners, but may also include cohabitants, and unmarried parents. Relatedly, the database may include different entries/boxes/designations for biological parents (sperm/egg donors, etc.), adopted parents, foster parents, surrogate parents, god parents, etc. In some examples, connections may focus on biological parents in order to capture a genome while still preserving record of valued family relationships that might not share blood.

In some examples, a website as described herein may provide the functionality of sending auto-generated messages to various members of the family, (e.g., by email or text message). For example, if information is missing from some particular area of a family tree, family members likely to know that information may be contacted in order to be informed of the database and benefits thereof, and potentially be requested to provide additional information. Similarly, if particular information may be useful from certain family members, such persons may also be contacted. As mentioned above, in some examples, particular family members may be contacted anonymously through for example an email that does not disclose particular identifying information of the recipient to the sender.

As described above, some object/benefits of the disclose may relate to identifying common ancestors, and sharing associated information. In one embodiment, a notification may be sent to offspring summarizing data regarding ancestors (geographical origin, etc.). In some examples, notification may have the purpose of gathering information regarding ancestors (address of a grave, photographs, written works, journal, address). In some examples, data regarding various deceased persons may be compared and similarities identified. Such similarities may in one example suggest a likelihood that two deceased persons knew each other. By way of one specific example, similarities in birth city and time period, or immigration records from similar dates (persons crossing an ocean on the same ship, soldiers having served in the same battalion, employees working at the same company or factory, students enrolled in the same institution or even the same classes, church members pertaining to the same congregation, etc.). Accordingly, some aspects of the disclosure may relate to determining whether separate persons' ancestors knew or likely each other.

A related object/benefit may be to identify the offspring of common ancestors. For example, one embodiment might include a means of identifying the geographic residences of all an individual ancestor's known offspring. In one embodiment, such means may include a representation of a globe and highlighted spots thereof corresponding to general places of residence. In some examples, a functional database may determine not only if one person is related, but also whether one person (person A) has a connection to someone who knows person A's relative.

For example, such connections may utilize data from other databases and potentially networking website (Facebook, LinkedIN, etc.), by determining associations/friends of a person and relatives of those associations friends. In one examples, contacts/connections may be imported from networking sites to supplement the functional database. For example, one person, Person C, may have a connection to Person A on Linkedin, and another connection to Person B on Facebook, and the functional database may be able to determine, using certain methods of confirming identities, that Person A is related to Person B. Moreover such a discovery may be made known to Person C. However, as explained above, whether and what information to present to Person C (and/or Persons A and B) may in some examples depend on levels of consent obtained by Persons A, B, and C.

In some examples, contacts/connections from networking sites of Family Member A may be imported and then pseudo-profiles may be created, which may be represented by an icon consisting of a thumbnail picture of a person and a name. Each relevant icon pertaining to, for example, family members, may be placed in a position on an inverted family tree (e.g., via "drag and drop" operations). Thus, an inverted family tree may be created in a convenient and seamless manner. Moreover, in some examples, once the icons have been dragged and dropped, the information may sync up and be updated to a main database, which may include the inverted family trees of other people, including family members of the Family Member A.

In some examples, the inverted family tree may allow knowing (at least generally) living relatives that were hitherto impossible or difficult to ascertain, and/or contacting such relative that were hitherto more difficult to reach. As should be apparent from this disclosure, in some examples certain functions may be performed allowing related individuals (perhaps distantly related individuals) to know they are related and how distantly related (e.g., seventh cousins) and who is their common ancestor. Some such embodiments may require the acquisition of certain genealogical records. The privacy of the information contained in the database may be governed according to privacy settings of the individuals' preferences.

These and other function may provide benefits to users/family members. For example, knowing the identities of family members may provide a greater or different sense of identity to particular persons who may otherwise be unaware of family members due for example to parents that have (whether intentionally or not) distanced children from extended family. In addition, examples of the database may provide a larger support network for family members to potentially take care of each other and provide support (for example emotional or temporal support) in times of need or crises. Some examples of database may assist in identifying donors with common biological traits that may help lessen the risk of an organ by rejected by a body. For instance, if person X is in need of a particular organ, the database may allow a related person who suddenly passes away to donate his/her organ to that family member. In addition, such a functional database may assist for purposes of networking, career moves, and life decisions. For example, a family member may be in need of an attorney, a real estate agent, a doctor, accountant, electrician etc., and such information may be available in the database as a source of referrals. In addition, if a prospective student is considering attending a particular school, examples of the database may include information regarding relatives who are alumni of that school, who may then be contacted for advice or recommendations regarding the school. In addition, examples of the database may have application relating to intestacy, which may for example help avoid situation where a deceased person has no living relative, and property of an estate may escheats to the government.

In some examples, the accuracy of the information provided in the database may be verified in a variety of ways. In one embodiment, the information identifying an individual may be verified by the individual her or himself (such verification being accomplished in manners known in particular arts). In another embodiment and/or the same embodiment, identifying information of an individual may be verified by a member of the individual's immediate family, and/or both (the individual her or himself and a member of the immediate family). In the game method 700, awards/recognitions (e.g., bonus points) may be bestowed for higher levels of verified accuracy of information.

In some examples, another manner of identification and specifically applicable for persons unable to conduct first person verification of information (e.g., for deceased individuals) may involve authentication using appropriate documents (birth certificates, photos of gravesites, etc.). In one embodiment, image files, etc., of such documents may also be added to the database. The authenticity of such documents may also be verified from a number of sources and/or persons. In the game method 700, higher points or other like awards/recognitions may be bestowed for verifying the authenticity of such documents. However, in some examples, use of such documents, and the identity of a common ancestor using such documents, or edits to the identifying information of the common ancestor, may not necessarily be needed to identify descendants to one another.

In one embodiment, persons may be able to disclose information about themselves and/or others: e.g., hair color, height, blood type, and including medical information such as diagnosed illness, etc. For example, in one embodiment, a photo may be uploaded and a program may determine certain characteristics traits of a person, which may include measurements of geometric facial features (distance between eyes, from mouth to nose, symmetry, etc.). In one example, a photo may be uploaded and trait identifier may automatically determine such traits. Some embodiments, the person submitting the photo may then be asked to verify particular information that the trait identifier gathers from the photo (e.g., hair color, eye color, etc.). In some examples, persons may disclose aptitudes, talents (e.g., musical, athletic), which may be included in the database.

In some examples, persons may disclose certain health related traits of either themselves or deceased persons (and potentially others). For example, one person may have high blood pressure, heart problems, obesity, breast cancer, autoimmune diseases, depression, high anxiety, ADHD, etc., etc., or may know that a deceased sibling or parent had similar traits. The person may disclose such information into the database and determine whether or not to share such information—and to whom, and under what conditions. For example, some persons may determine not to share such information until after death. Others may decide to share such information in certain more or less anonymous ways. For example, some medical information may be "de-identified" with particular persons, and then shared. For instance, consider a large pool of family members related to a common ancestor. Person A may be provided a summary of health risks based on information relating to traits of the members of the pool. However, the summary may not include any identifying information of individuals of the members of the pool. Rather, the summary may simply indicate for example, areas of concern, and in some cases certain percentage probabilities of risks.

In one embodiment, one manner of gathering information and also in assisting in verifying that individuals share common blood ancestry, may be through using DNA samples and identifying relevant gene "markers" thereof. In another embodiment, databases may include gene maps of related individuals and also a means for assimilating said information in useful ways. For example, the advantages of gene mapping of groups of related individuals and assimilation of such data may include the availability of beneficial information to individuals, including regarding genetic predispositions to certain diseases, syndromes, disorders, conditions, etc. In some examples, techniques may include identifying different mutations affecting particular genes; and/or identifying a particular phenotype(s) and then linking with a gene(s), and then potentially determining (e.g., within a certain degree of probability) the mutation(s) that affected the gene(s). Such identifying may either by persons disclosing information and/or by other parties systems. In addition, persons may disclose certain environmental factors, which may also be used when analyzing for example the causes of disease conditions/disorders syndromes. In some examples, analysis may include distinguishing between disease causing mutations and similar mutations that are false positives. In some examples, the distinction may be reflected in certain probabilities (e.g., gene A may be linked with disease 1, with a base likelihood of being a false positive of 30%, which probability is increased by 5% based on other genetic factors (sex, race, combination with other genes), and decrease 5% by particular environmental factors).

Gene mapping analysis may have applications for monogenic disorders, complex disorders, genomic disorders (e.g., affecting chromosomal abnormalities), and environmental diseases. For example, a genetic marker locus may be linked with a probability of risk for a disease (e.g., Huntington's disease and OMIM #143100). As previously mentioned, certain genes may cause different reactions to the same disease, whether an environmentally-caused or otherwise epigenetic disease (e.g., CCR5 for HIV-2, FUT2 for norovirus, DARC for certain malaria pathogens) or genetic disease. The size and rarity of alleles may also be considered in the analysis.

In addition to the aforementioned benefits, such databases including gene mapping information may be useful to persons considering mating and producing offspring, to determine what genes their offspring might potentially inherit (ranging from simple visible characteristics such as height, hair and eye color (e.g., red hair), etc., to more complex and less evidence characteristics such as inherited bi-polarity, mental illness, etc.). One embodiment of the method and system described herein may include the generation of charts showing the probability that offspring will inherit certain genes and/or characteristics. In one embodiment, the gene mapping information may be used to generate a graphic representation of what offspring could potentially look like. In one embodiment, at least some of the aforementioned functions may be performed by an offspring gene predictor. In one example, genes of a potential father and/or potential mother may be analyzed for consulting purposes regarding offspring. For example, it might be determined that a father has a MECP2 gene at a particular location on the X chromosome, which may potentially be passed on to female offspring, causing Rett syndrome (or intellectual disability in male offspring). In such instances, particular treatment/actions early on in the life/development of female offspring may help mitigate harmful effects/phenotypes. For example, certain treatment may involve at least in part selective expression of a health X chromosome rather than preferential expression of the X chromosome copy with mutant MECP2. In another example, where a predisposition to phenylketonuria is predicted, an newborn may be subject to heightened screenings and/or provided a phenylalanine-less diet.

In another example, genetic predisposition to certain illnesses based on race may be taken into account (e.g., sickle cell anemia for African population, including the heterozygous condition, which may provide benefits against malaria, mutant HBB gene, etc., Tay-Sachs disease for Ashkenazi population, cystic fibrosis for northern European ancestry, etc.). Other genetic diseases, for example, which may be of interest may include (but not limited to) Hemophilia A, Hunter syndrome, Neurofibromatosis type 1, Bartter syndrome type III, Spinal muscular atrophy, Gaucher disease, thalassemia, etc. A mother's mitochondrial DNA might also be analyzed. In addition, analysis may also include somatic, mosaic mutations and related diseases/syndromes—e.g., Sturge-Weber, Proteus syndrome, and McCune-Albright Syndrome) to the extent such may be passed on to progeny.

As explained above, the methods and systems described herein may take various received information relating to such health conditions, and compute probabilities of risk. Such information may also be presented in a summary to a relevant person. In some examples, and depending on characteristics of a particular trait, a probability of risk may be increased where a person's direct ancestors, or siblings with identically shared ancestry, have certain health conditions. In addition, where a particular health trait is of a distant relative, a probability of risk may be decreased accordingly. In some examples, when generating a summary, the system and methods described herein may involve computing probabilities of risk by taking into account the health traits of many different family members, taking into account unshared ancestry and determining within a range of probabilities what particular lines carry certain genes.

In some examples, based on information specifically relevant to an individual's probabilities of risks, a summary may further include proactive steps that may be taken to minimize risks. For example, if a person has a high probability of risk of certain heart-related diseases, a particular diet may be suggested that is known to alleviate such risk. Similarly, if a person has a high probability of certain autoimmune diseases, the summary may include information on the autoimmune protocol diet. In addition, in some examples, the summary may include information about certain test (and relatedly, a biopsy) that may be performed to determine whether a person indeed has a particular condition. In some examples, the summary may include a referral list of physicians who may be qualified to provide medical advice relating to the summary. In some examples, the list of physicians may include specialists in a particular region associated with the individual receiving the summary. In addition, for example, the summary may include for more rare risks national or global experts for a particular condition. In some examples, the list may take into account a particular individual's health insurance and then provide a list of physicians that accept the individual's health insurance.

In any case, the information generated by the method and systems described above alone may provide a sufficient incentive for individuals to submit and provide the information and consent to providing information. However, additional and potentially monetary-related incentives may also be provided. For example, some gene mapping tests may be provided to certain individuals for free. In addition, gift certificates or other financial incentives may also be provided to individuals who provide certain information for themselves or who "refer" others (to play the game, in the game embodiment). Such gift certificates or financial incentives may also be directed to nonprofits organizations, etc.

The provider of such financial incentives may include a variety of sources. However, in one embodiment, such a financial incentive provider may include health care providers and/or research institutions that may use the information in the databases in potentially useful ways. For example, by proactively addressing potential health risks, the costs of treatment may be minimized for insurers, and therefore some insurers may desire to encourage participation by insureds in some a database. In one embodiment some such parties may also assist in the assimilating of such information. Similar to methods describe above, in some embodiments, information may be shared by others without compromising the specific identifying information of individuals. For example, consider the database of one larger group of related individuals (and in the game embodiment, a "high level" of achievement): the genetic mapping information may not be tied to a specific individual but rather may be disclosed in a more general manner and attributed to the whole group.

In other aspects or embodiments where the gene mapping information is not intended to be utilized, a method, system, etc., may also include information of a variety of interrelated individuals not necessarily related closely by blood. The method and/or system of the disclosure may have a number of benefits and applications that will be appreciated by those of ordinary skill in the relevant arts.

Figure 9:
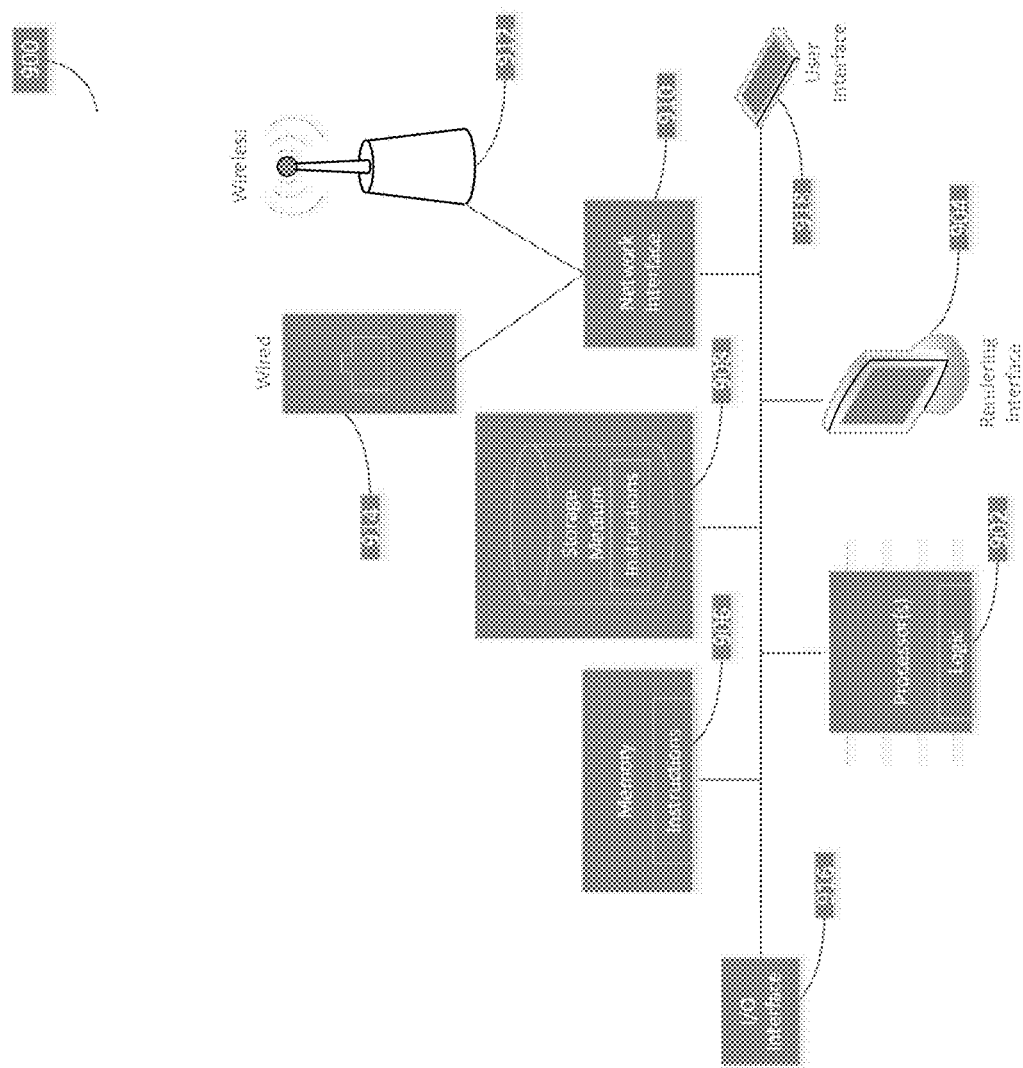
FIG. 9 is a schematic diagram of a computing system, in accordance with some aspects of the present disclosure.

FIG. 9 is a schematic diagram of a computing system 900 in accordance with some aspects of the present disclosure. The computing system 900 can be viewed as an information passing bus that connects various components. In the embodiment shown, the computing system 900 includes a processor 902 having logic 902 for processing instructions. Instructions can be stored in and/or retrieved from memory 906 and a storage device 908 that includes a computer-readable storage medium. The memory 906 may also include any combination of various levels of memory/storage including, but not limited to, read-only memory (ROM) having embedded software instructions (e.g., firmware), random access memory (e.g., dynamic random access memory (DRAM)), cache, buffers, etc. In some embodiments, the memory/storage 906 may be shared among various processors and not necessarily just processor 902) or dedicated to particular processors.

Instructions and/or data can arrive from a network interface 910 that can include wired 914 or wireless 912 capabilities. Instructions and/or data can also come from an I/O interface 916 that can include such things as expansion cards, secondary buses (e.g., USB, etc.), devices, etc. A user can interact with a computing system 900 though user interface devices 918 and a rendering system 904 that allows the computer to receive and provide feedback to the user.

Although not expressly indicated with reference numbers, specific electronic device circuitry may be operable to perform one or more methods described herein. As used herein, the term "circuitry" may refer to, be part of, or include an application specific integrated circuit (ASIC), an electronic circuit, a processor (shared, dedicated, or group), and/or memory (shared, dedicated, or group) that execute one or more software or firmware programs, a combinational logic circuit, and/or other suitable hardware components that provide the described functionality. In some embodiments, the circuitry may be implemented in, or functions associated with the circuitry may be implemented by, one or more software or firmware modules. In some embodiments, circuitry may include logic, at least partially operable in hardware. Embodiments described herein may be implemented into a system using suitably configured hardware and/or software. By way of non-limiting example, the circuitry may further include one or more single-core or multi-core processors. The processor(s) (such as for example processor 902) may include any combination of general-purpose processors and dedicated processors (e.g., graphics processors, application processors, etc.). The processor(s) may be operably coupled and/or include memory/storage (such as for example memory 906), and may be configured to execute instructions stored in the memory storage to enable various applications and/or operating systems to run on the system.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

The various illustrative blocks and components described in connection with this disclosure may be implemented or performed with a general-purpose processor, a digital signal processor (DSP), an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, and/or state machine. A processor may also be implemented as a combination of computing devices, e.g., a combination of a DSP and a microprocessor, multiple microprocessors, one or more microprocessors in conjunction with a DSP core, and/or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

Some aspects of the disclosure may involve computer-readable media. Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media may include RAM, ROM, EEPROM, flash memory, CD-ROM, DVD, or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

Furthermore, while various embodiments have been described and/or illustrated here in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may permit and/or instruct a computing system to perform one or more of the exemplary embodiments disclosed here.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:
1. A computer-implemented method of diagnosing family traits, comprising:
utilizing computer-readable media that, as a result of being executed by one or more processors of a computer system, cause the computer system to:
identify, via at least in part the one or more processors, a first person based at least in part on input provided by the first person via at least one website;
record information, via at least in part the one or more processors, regarding the identified first person in at least one database, based at least in part on the identifying and on the input provided by the first person, wherein the recorded information comprises first data associated with at least one ancestor of the first person, and wherein the at least one database is in electronic communication with the computer system and the at least one website;
send, via at least in part the one or more processors, on behalf of the first person, an invitation to a second person associated with the at least one database, wherein the invitation comprises a first electronic communication;
share, via at least in part the one or more processors, based at least in part on the sending, access to the at least one database with the second person;
identify, via at least in part the one or more processors, based at least in part on the shared access, the second person;
record, via at least in part the one or more processors, based at least in part on the identifying the second person, information regarding the identified second person in the at least one database, and information regarding a third person previously unknown to the first person;
determine, via at least in part the one or more processors, based at least in part on the recording the information regarding the identified second person, that the first person and the second person and the third person and a fourth person are related and how the first person and the second person and the third person and the fourth person are related, and wherein the first person and the second person and the third person and the fourth person are related by having in common the at least one ancestor, wherein the first person, the second person, the third person, and the at least one ancestor comprise identified family members;

determine, via at least in part the one or more processors, at least one shared non-biological trait between the first person, the second person, the third person, and the fourth person, wherein the at least one shared non-biological trait is distinct from how the first person and the second person and the third person and the fourth person are related;

update, via at least in part the one or more processors, the recorded information regarding the first person in the at least one database, wherein the updated recorded information comprises second data that includes the at least one shared non-biological trait;

provide, via at least in part the one or more processors and the at least one website, and based at least in part on the updating, to at least one of the first person, the second person, the third person, or the fourth person, a summary that includes the updated recorded information;

determine, via at least in part the one or more processors, that some information of the at least one database is incomplete;

identify, via at least in part the one or more processors, a fourth person associated with the incomplete information; and send a message, via at least in part the one or more processors, to the fourth person associated with completing the incomplete information, wherein the message comprises a second electronic communication associated with the at least one website.

2. The method of claim 1, wherein the recorded information regarding the identified first person is recorded in a first database of the at least one database associated with a first website of the least one website, and at least one of the identifying the first person or the identifying the second person comprises importing data from a second database of the at least one database associated with a second website of the least one website, wherein the second database is in electronic communication with the computer system.

3. The method of claim 2, wherein the second database is related to at least one of: a social networking database or a genealogical database.

4. The method of claim 1, further comprising authenticating the recorded information.

5. The method of claim 1, wherein the identified family members have different classifications.

6. The method of claim 5, wherein the classifications comprise:
different levels of family members.

7. The method of claim 6, wherein the levels of family members comprise:
level one family members comprising an immediate family, level two family members having at least one shared grandparent with the level one family members, and level three family members having at least one shared great-grandparent with the level one family members;
wherein identifying family members comprises:
identifying level one family members before identifying level two family members, and identifying level two family members before identifying level three family members; and
wherein recording information comprises:
recording information regarding the identified level one family members before recording information regarding the identified level two family members, and recording information regarding the identified level two family members before recording information regarding the identified level three family members.

8. The method of claim 7, wherein the levels of family members include at least level four family members and level five members; and
the at least one database includes:
recorded information of identified family members of different family groups; and
wherein, the recorded information of identified family members of different family groups is mergeable upon discovering a common ancestor between different groups.

9. The method of claim 1, wherein the updating the recorded information comprising the second data associated with the at least one non-biological trait-is based at least in part on the recorded information regarding the third person.

10. The method of claim 1, wherein determining traits comprises at least one of identified family members responding to a questionnaire, or a third party supplying non-biological traits regarding identified family members.

11. The method of claim 10, wherein the third party comprises at least one of:
a medical provider or an insurer.

12. The method of claim 1, wherein the at least one non-biological trait comprises at least one of:
a socio-economic characteristic, an ideological characteristic, or a life decision.

13. The method of claim 12, wherein the socio-economic characteristic, ideological characteristic, and life decision comprises at least one of: an education level, a profession, a political affiliation, a religious persuasion, an associated organization, a marital status, a criminal history, an alma matter, or a post of present domicile.

14. The method of claim 1, further comprising:
organizing the information regarding the identified family members according to family lines and shared common ancestors.

15. The method of claim 14, wherein identified family members have access to the identities of other identified family members.

16. The method of claim 15 further comprising:
a potential family member inputting information in the at least one database, and determining that the potential family member is a family member.

17. A computer-implemented method of diagnosing family traits, comprising:
utilizing computer-readable media that, as a result of being executed by one or more processors of a computer system, cause the computer system to:
identify, via at least in part the one or more processors, a first person based at least in part on input provided by the first person via at least one website;
record information, via at least in part the one or more processors, regarding the identified first person in at least one database, based at least in part on the identifying and on the first input provided by the first person, wherein the recorded information comprises first data associated with at least one ancestor of the first person, and wherein the at least one database is in electronic communication with the computer system, and the at least one website;
send, via at least in part the one or more processors, on behalf of the first person, an invitation to a second person associated with the at least one database, wherein the invitation comprises a first electronic communication;

share, via at least in part the one or more processors, based at least in part on the sending, access to the at least one database with the second person;

identify, via at least in part the one or more processors, based at least in part on the shared access, the second person;

record, via at least in part the one or more processors, based at least in part on the identifying the second person, information regarding the identified second person in the at least one database, and information regarding a third person previously unknown to the first person;

determine, via at least in part the one or more processors, based at least in part on the recording the information regarding the identified second person, that the first person and the second person and the third person have in common the at least one ancestor, wherein the first person, the second person, the third person, and the at least one ancestor comprise identified family members;

determine, via at least in part the one or more processors, a place of work associated with at least one of the first person, the second person, or the third person;

identify, via at least in part the one or more processors, at least one friend associated with at least one of the first person, the second person, or the third person, wherein the at least one friend is distinct from the at least one ancestor;

match, via at least in part the one or more processors, the determined place of work associated with the at least one of the first person, the second person, the third person with the identified at least one friend, wherein the at least one of the first person, the second person, or the third person for which the place of work is determined is different from the at least one of the first person, the second person, the third person for which the at least one friend was identified;

update, via at least in part the one or more processors, at least one of the recorded information regarding the first person, the recorded information regarding the second person, and recorded information regarding the third person, in the at least one database, wherein the updated recorded information comprises second data including the determined place of work, and the at least one identified friend; and provide, via at least in part the one or more processors and the at least one website, to at least one of the first person, the second person, or the third person, a summary that includes the updated recorded information.

18. A computer-implemented method of diagnosing family traits, comprising:

utilizing computer-readable media that, as a result of being executed by one or more processors of a computer system, cause the computer system to:

identify, via at least in part the one or more processors, a first person based at least in part on a first input provided by the first person via at least one website;

record information, via at least in part the one or more processors, regarding the identified first person in a at least one database, based at least in part on the identifying and on the input provided by the first person, wherein the recorded information comprises first data associated with at least one ancestor of the first person, and wherein the at least one database is in electronic communication with the computer system, and the at least one website;

send, via at least in part the one or more processors, on behalf of the first person, an invitation to a second person associated with the at least one database, wherein the invitation comprises a first electronic communication;

share, via at least in part the one or more processors, based at least in part on the sending, access to the at least one database with the second person;

identify, via at least in part the one or more processors, based at least in part on the shared access, the second person;

record, via at least in part the one or more processors, based at least in part on the identifying the second person, information regarding the identified second person in the at least one database, and information regarding a third person previously unknown to the first person;

determine, via at least in part the one or more processors, based at least in part on the recording the information regarding the identified second person, that the first person and the second person and the third person and a fourth person are related and how the first person and the second person and the third person and the fourth person are related, and wherein the first person and the second person and the third person and the fourth person are related by having in common the at least one ancestor, wherein the first person, the second person, the third person, and the at least one ancestor comprise identified family members;

determine, via at least in part the one or more processors, at least one shared trait between at least two of the first person, the second person, and the third person and the fourth person, wherein the at least one shared trait is distinct from how the first person and the second person and the third person and the fourth person are related;

compare, via at least in part the one or more processors, the at least one shared trait with a trait of a fifth person, wherein the trait of the fifth person is the same as or different from the at least one shared trait;

determine, via at least in part the one or more processors, based at least in part on the comparing, a probability that an offspring between the fifth person and the first person, the second person, the third person, or the fourth person will have the at least one shared trait;

update, via at least in part the one or more processors, at least one of the recorded information regarding the first person, the recorded information regarding the second person, recorded information regarding the third person, and recorded information regarding the fourth person, in the at least one database, wherein the updated recorded information comprises second data that includes the at least one shared trait and the determined probability; and provide, via at least in part the one or more processors and the at least one website, to at least one of the first person, the second person, the third person, or the fourth person, a summary that includes the updated recorded information.

19. The method of claim 18, wherein the at least one shared trait comprises a biological characteristic, and wherein the biological characteristic comprises at least one of:

a physical characteristic, a race, a gender, a gene marker, and an illness, disease, or disorder.

20. The method of claim 19, wherein the illness, disease, or disorder comprises at least one of:

Thalassaemia, sickle cell anemia, haemophilia, cystic fibrosis, Tay Sachs disease, fragile X syndrome, Huntington's disease, Angelman Syndrome, diabetes, cancer, alcoholism, auto-immune diseases, or schizophremia.

* * * * *